United States Patent
Olenik et al.

(10) Patent No.: US 9,926,305 B2
(45) Date of Patent: *Mar. 27, 2018

(54) SALTS

(71) Applicant: Bayer Pharma Aktiengesellschaft, Berlin (DE)

(72) Inventors: Britta Olenik, Bottrop (DE); Birgit Keil, Düsseldorf (DE); Martin-Holger Hinz, Hückeswagen (DE); Chantal Fürstner, Mülheim/Ruhr (DE); Mario Jeske, Solingen (DE); Jens Ackerstaff, Düsseldorf (DE)

(73) Assignee: Bayer Pharma Aktiengesellschaft, Berlin (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/035,165

(22) PCT Filed: Nov. 5, 2014

(86) PCT No.: PCT/EP2014/073801
§ 371 (c)(1),
(2) Date: May 6, 2016

(87) PCT Pub. No.: WO2015/067652
PCT Pub. Date: May 14, 2015

(65) Prior Publication Data
US 2016/0289220 A1     Oct. 6, 2016

(30) Foreign Application Priority Data
Nov. 8, 2013   (EP) ..................................... 13192177

(51) Int. Cl.
| | | |
|---|---|---|
| *A61K 31/506* | (2006.01) | |
| *C07D 413/04* | (2006.01) | |
| *C07C 229/26* | (2006.01) | |

(52) U.S. Cl.
CPC .......... *C07D 413/04* (2013.01); *C07C 229/26* (2013.01)

(58) Field of Classification Search
CPC .................................................... C07D 413/04
See application file for complete search history.

(56) References Cited

U.S. PATENT DOCUMENTS

| | | | | |
|---|---|---|---|---|
| 9,481,672 B2 * | 11/2016 | Furstner | ............... | C07D 413/14 |
| 2004/0019068 A1 | 1/2004 | Miyazaki et al. | | |
| 2016/0244415 A1 * | 8/2016 | Furstner | ............... | C07D 403/12 |
| 2017/0020875 A1 * | 1/2017 | Furstner | ............... | C07D 413/14 |
| 2017/0020876 A1 * | 1/2017 | Furstner | ............... | C07D 413/14 |

FOREIGN PATENT DOCUMENTS

| | | | | |
|---|---|---|---|---|
| WO | 201316749 A1 | 11/2013 | | |
| WO | WO 2013167495 A1 * | 11/2013 | ........... | C07D 413/14 |
| WO | WO 2015067651 A1 * | 5/2015 | ........... | C07D 403/12 |

OTHER PUBLICATIONS

S.L. Morissette et al., 56 Advanced Drug Delivery Reviews, 275-300, 276 (2004).*
S. H. Neau, Pharmaceutical Salts, in Water-Insoluble Drug Formulation 417, 429 (R. Liu ed., CRC Press, 2008).*
S. Badaway et al., Salt Selection for Pharmaceutical Compounds, in Preformulation in Solid Dosage Form Dev. 63 (M. Adeyeye ed., 2008).*
R.J. Bastin et al., Salt Selection and Optimization Procedures for Pharmaceutical New Chemical Entities, 4 Organic Process Res. Dev. 427 (2000).*
P.L. Gould, Salt Selection for Basic Drugs, 33 Int. J. Therapeutics 201, 217 (1986).*
K. R. Morris et al., An Integrated Approach to the Selection of Optimal Salt Form for a New Drug Candidate, 105 Int'l. J. Pharm. 209 (1994).*
K. Chow et al., Engineering of Pharmaceutical Materials: an Industrial Perspective, 97 J. Pharmaceutical Sciences, 2855 (2008).*
L.D. Bighley et al., Salt Forms and Absorption, in 13 Encyclopedia of Pharmaceutical Technology 453 (M Swarbrick and J. Boylan eds., 1996).*
European Patent Office, Written Opinion for International Patent Application No. PCT/EP2014/073801, dated May 14, 2015, 5 pages.
European Patent Office, International Search Report (with English translation) for International Patent Application No. PCT/EP2014/073801, dated Nov. 28, 2014, 5 pages.
Senda, et al., "Pyrimidine Derivatives and Related Compounds. XVI. Synthesis of 1,3-Disubstituted 5-Cyanouracil Derivatives and Related Compounds", Chem. Pharm. Bull., 20(7), 1972, pp. 1380-1388.

* cited by examiner

*Primary Examiner* — Alexander R Pagano
(74) *Attorney, Agent, or Firm* — Morrison & Foerster LLP

(57) ABSTRACT

Salts of 1-(3-methyl-2-oxo-2,3-dihydro-1,3-benzoxazol-6-yl)-2,4-dioxo-3-[(1R)-4-(trifluoromethyl) -2,3-dihydro-1H-inden-1-yl]-1,2,3,4-tetrahydropyrimidine-5-carboxylic acid of the formula (I), in particular amino acid salts such as the lysine salt and alkali metal salts such as the sodium salt and the potassium salt, processes for their preparation, medicaments comprising them and their use for controlling diseases.

21 Claims, 3 Drawing Sheets

SALTS

CROSS-REFERENCE TO RELATED APPLICATIONS

This application is a U.S. national phase application of International Patent Application No. PCT/EP2014/073801, filed Nov. 5, 2014 and titled SALTS OF 1-(3-METHYL-2-OXO)-2,3-DIHYDRO-1,3-BENZOXAZOL-6-YL)-2,4-DI-OXO-3-[(1R) -4-(TRIFLUORMETHYL)-2,3-DIHYDRO-1H-INDEN-1-YL]-1,2,3,4-TETRAHYDROPYRIMIDIN-5-CARBOXYLIC ACID, which claims priority to European Patent Application No. 13192177.7, filed Nov. 8, 2013 and titled SALTS OF 1-(3-METHYL-2-OXO-2,3-DIHYDRO-1,3-BENZOXAZOL-6-YL)-2,4-DIOXO-3-[(1R)-4-(TRIF-LUORMETHYL)-2,3-DIHYDRO-1H-INDEN-1-YL]-1,2,3,4-TETRAHYDROPYRIMIDIN-5-CARBOXYLIC ACID, the contents of both of which are incorporated herein by reference in their entirety.

The invention relates to novel salts of 1-(3-methyl-2-oxo-2,3-dihydro-1,3-benzoxazol-6-yl)-2,4-dioxo-3-[(1R)-4-(tri-fluoromethyl)-2,3-dihydro-1H-inden-1-yl]-1,2,3,4-tetrahy-dropyrimidine-5-carboxylic acid of the formula (I), in particular to amino acid salts such as the lysine salt and to alkali metal salts such as the sodium salt and the potassium salt, to processes for their preparation, to medicaments comprising them and their use for controlling diseases.

1-(3-Methyl-2-oxo-2,3-dihydro-1,3-benzoxazol-6-yl)-2,4-dioxo-3-[(1R)-4-(trifluoromethyl)-2,3-dihydro-1H-inden-1-yl]-1,2,3,4-tetrahydropyrimidine-5-carboxylic acid, its preparation and its use as chymase inhibitor is described in the patent application PCT/EP2013/059286 (see Example 189) and corresponds to the compound of the formula (I):

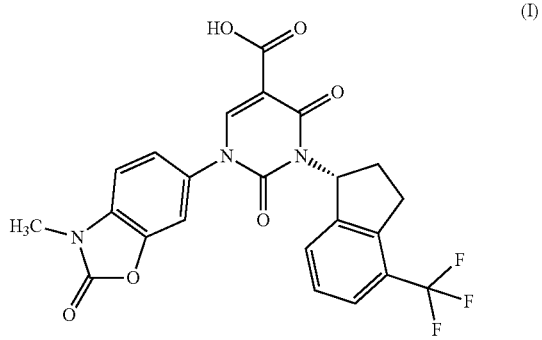 [SMILES: Cn1c(=O)oc2cc(-n3cc(C(=O)O)c(=O)n([C@@H]4CCc5c4cccc5C(F)(F)F)c3=O)ccc21]

Hereinbelow, the compound of the formula (I) is referred to as free acid.

It has now been found that, for some applications, the free acid has insufficient solubility and is therefore not unconditionally suitable for use in formulations.

Surprisingly, we have now found novel salts. These salts have markedly different and in each case characteristic X-ray diffractograms (Table 1, FIGS. 1, 2 and 3).

The present invention provides the compound of the formula (I) in the form of its amino acid salts and alkali metal salts.

The present invention provides the compound of the formula (I) in the form of its lysine salt, in particular in the form of its L-lysine salt, or in the form of its sodium salt or potassium salt.

The present invention provides the compound of the formula (I) in the form of its L-lysine salt which, in the X-ray diffractogram, has essentially the following preferred peak maximum of the 2 theta angle at 16.9.

The present invention preferably provides the compound of the formula (I) in the form of its L-lysine salt which, in the X-ray diffractogram, has essentially the following preferred peak maxima of the 2 theta angle at 16.9, 22.3 and 20.0.

The present invention furthermore preferably provides the compound of the formula (I) in the form of its L-lysine salt which, in the X-ray diffractogram, has essentially the following preferred peak maxima of the 2 theta angle at 16.9, 22.3, 20.0, 16.7, 19.2, , 10.9 and 12.2.

The present invention furthermore preferably provides the compound of the formula (I) in the form of its L-lysine salt which, in the X-ray diffractogram, has essentially the following preferred peak maxima of the 2 theta angle at 16.9, 22.3, 20.0, 16.7, 19.2, , 10.9, 12.2, 9.9 and 21.6.

Moreover, the present invention provides the compound of the formula (I) in the form of its sodium salt which, in the X-ray diffractogram, has essentially the following preferred peak maximum of the 2 theta angle at 17.6.

The present invention preferably provides the compound of the formula (I) in the form of its sodium salt which, in the X-ray diffractogram, has essentially the following preferred peak maxima of the 2 theta angle at 17.6, 17.9 and 19.1.

The present invention furthermore preferably provides the compound of the formula (I) in the form of its sodium salt which, in the X-ray diffractogram, has essentially the following preferred peak maxima of the 2 theta angle at 17.6, 17.9, 19.1, 18.1, 12.8, 5.9 and 18.9.

The present invention furthermore preferably provides the compound of the formula (I) in the form of its sodium salt which, in the X-ray diffractogram, has essentially the following preferred peak maxima of the 2 theta angle at 17.6, 17.9, 19.1, 18.1, 12.8, 5.9, , 18.9, 29.0 and 19.6.

Moreover, the present invention provides the compound of the formula (I) in the form of its potassium salt which, in the X-ray diffractogram, has essentially the following preferred peak maximum of the 2 theta angle at 23.7.

The present invention preferably provides the compound of the formula (I) in the form of its potassium salt which, in the X-ray diffractogram, has essentially the following preferred peak maxima of the 2 theta angle at 23.7, 15.3 and 20.5.

The present invention furthermore preferably provides the compound of the formula (I) in the form of its potassium salt which, in the X-ray diffractogram, has essentially the following preferred peak maxima of the 2 theta angle at 23.7, 15.3, 20.5, 10.4, , 30.0, 21.7 and 6.00.

The present invention furthermore preferably provides the compound of the formula (I) in the form of its potassium salt which, in the X-ray diffractogram, has essentially the following preferred peak maxima of the 2 theta angle at 23.7, 15.3, 20.5, 10.4, , 30.0, 21.7, 6.0, 19.8 and 18.0.

General aspects in connection with the present invention are pharmacological properties, processability, preparation process, side-effect profile, stability and pharmacological activity in particular of the salt with L-lysine of the compound of the formula (I).

Surprisingly, the L-lysine salt and the sodium and potassium salt of the compound of the formula (I) are crystalline and, even after processing via suspensions, storage-stable. Accordingly, they are particularly suitable for use in pharmaceutical formulations such as suspensionen or creams, but also in other preparations prepared via the suspended active compound, such as, for example, in the case of wet granulation or wet grinding.

In pharmaceutical formulations, the salts according to the invention of the compound of the formula (I), in particular the L-lysine salt and the sodium and potassium salt, are employed in high purity. For reasons of stability, a pharmaceutical formulation comprises mainly a salt of the compound of the formula (I), in particular either the L-lysine salt or the sodium or potassium salt, and no greater proportions of any other form of the compound of the formula (I). Preferably, the medicament comprises more than 90 percent by weight, particularly preferably more than 95 percent by weight, of the compound of the formula (I) in the form of the corresponding salt, based on the total amount of the compound of the formula (I) present.

The salts of the invention have valuable pharmacological properties and can be used for treatment and/or prophylaxis of diseases in humans and animals The salts of the invention are chymase inhibitors and are therefore suitable for treatment and/or prophylaxis of cardiovascular, inflammatory, allergic and/or fibrotic disorders.

In the context of the present invention, disorders of the cardiovascular system or cardiovascular disorders are understood to mean, for example, the following disorders: acute and chronic heart failure, arterial hypertension, coronary heart disease, stable and unstable angina pectoris, myocardial ischemia, myocardial infarction, shock, atherosclerosis, cardiac hypertrophy, cardiac fibrosis, atrial and ventricular arrhythmias, transitory and ischaemic attacks, stroke, pre-eclampsia, inflammatory cardiovascular disorders, peripheral and cardiac vascular disorders, peripheral perfusion disorders, arterial pulmonary hypertension, spasms of the coronary arteries and peripheral arteries, thromboses, thromboembolic disorders, edema development, for example pulmonary edema, cerebral edema, renal edema or heart failure-related edema, and restenoses such as after thrombolysis treatments, percutaneous transluminal angioplasty (PTA), transluminal coronary angioplasty (PTCA), heart transplants and bypass operations, and micro- and macrovascular damage (vasculitis), reperfusion damage, arterial and venous thromboses, microalbuminuria, myocardial insufficiency, endothelial dysfunction, peripheral and cardiac vascular disorders, peripheral perfusion disorders, heart failure-related edema, elevated levels of fibrinogen and of low-density LDL and elevated concentrations of plasminogen activator/inhibitor 1 (PAI-1).

In the context of the present invention, the term "heart failure" also includes more specific or related types of disease, such as acutely decompensated heart failure, right heart failure, left heart failure, global failure, ischaemic cardiomyopathy, dilated cardiomyopathy, congenital heart defects, heart valve defects, heart failure associated with heart valve defects, mitral valve stenosis, mitral valve insufficiency, aortic valve stenosis, aortic valve insufficiency, tricuspid stenosis, tricuspid insufficiency, pulmonary valve stenosis, pulmonary valve insufficiency, combined heart valve defects, myocardial inflammation (myocarditis), chronic myocarditis, acute myocarditis, viral myocarditis, diabetic heart failure, alcoholic cardiomyopathy, cardiac storage disorders, and diastolic and systolic heart failure.

The salts according to the invention are further suitable for the prophylaxis and/or treatment of polycystic kidney disease (PCKD) and of the syndrome of inappropriate ADH secretion (SIADH). The salts of the invention are also suitable for treatment and/or prophylaxis of kidney disorders, in particular of acute and chronic renal insufficiency and acute and chronic renal failure.

In the context of the present invention, the term "acute renal insufficiency" encompasses acute manifestations of kidney disease, of kidney failure and/or renal insufficiency with and without the need for dialysis, and also underlying or related renal disorders such as renal hypoperfusion, intradialytic hypotension, volume deficiency (e.g. dehydration, blood loss), shock, acute glomemlonephritis, hemolytic-uremic syndrome (HUS), vascular catastrophe (arterial or venous thrombosis or embolism), cholesterol embolism, acute Bence-Jones kidney in the event of plasmacytoma, acute supravesicular or subvesicular efflux obstructions, immunological renal disorders such as kidney transplant rejection, immune complex-induced renal disorders, tubular dilatation, hyperphosphatemia and/or acute renal disorders characterized by the need for dialysis, including in the case of partial resections of the kidney, dehydration through forced diuresis, uncontrolled blood pressure rise with malignant hypertension, urinary tract obstruction and infection and amyloidosis, and systemic disorders with glomerular factors, such as rheumatological-immunological systemic disorders, for example lupus eiythematodes, renal artery thrombosis, renal vein thrombosis, analgesic nephropathy and renal tubular acidosis, and X-ray contrast agent- and medicament-induced acute interstitial renal disorders.

In the context of the present invention, the term "chronic renal insufficiency" encompasses chronic manifestations of kidney disease, of kidney failure and/or renal insufficiency with and without the need for dialysis, and also underlying or related renal disorders such as renal hypoperfusion, intradialytic hypotension, obstructive uropathy, glomerulopathy, glomerular and tubular proteinuria, renal edema, hematuria, primary, secondary and chronic glomemlonephritis, membranous and membranoproliferative glomerulonephritis, Alport syndrome, glomemlosclerosis, tubulointerstitial disorders, nephropathic disorders such as primary and congenital kidney disease, renal inflammation, immunological renal disorders such as kidney transplant rejection, immune complex-induced renal disorders, diabetic and non-diabetic nephropathy, pyelonephritis, renal cysts, nephrosclerosis, hypertensive nephrosclerosis and nephrotic syndrome, which can be characterized diagnostically, for example, by abnormally reduced creatinine and/or water excretion, abnormally elevated blood concentrations of urea, nitrogen, potassium and/or creatinine, altered activity of renal enzymes, for example glutamyl synthetase, altered urine osmolarity or urine volume, elevated microalbuminuria, macroalbuminuria, glomerular and arteriolar lesions, tubular dilatation, hyperphosphatemia and/or the need for dialysis, and in the event of renal cell carcinoma, after partial resections of the kidney, dehydration through forced diuresis, uncontrolled blood pressure rise with malignant hypertension, urinary tract obstruction and infection and amyloidosis, and systemic disorders with glomerular factors, such as rheumatological-immunological systemic disorders, for example lupus erythematodes, and also renal artery stenosis, renal artery thrombosis, renal vein thrombosis, analgesic nephropathy and renal tubular acidosis. In addition, X-ray contrast agent- and medicament-induced chronic interstitial renal disorders, metabolic syndrome and dyslipidemia. The present invention also encompasses the use of the compounds of the invention for the treatment and/or prophylaxis of sequelae of renal insufficiency, for example pulmonary edema, heart failure, uremia, anemia, electrolyte disorders (for example hyperkalemia, hyponatremia) and disorders in bone and carbohydrate metabolism.

In addition, the salts according to the invention are also suitable for treatment and/or prophylaxis of pulmonary arterial hypertension (PAH) and other forms of pulmonary hypertension (PH), of chronic obstructive pulmonary disease (COPD), of acute respiratory distress syndrome (ARDS), of acute lung injury (ALI), of alpha-1-antitrypsin deficiency (AATD), of pulmonary fibrosis, of pulmonary emphysema (for example pulmonary emphysema caused by cigarette smoke), of cystic fibrosis (CF), of acute coronary syndrome (ACS), heart muscle inflammation (myocarditis) and other autoimmune cardiac disorders (pericarditis, endocarditis, valvolitis, aortitis, cardiomyopathy), cardiogenic shock, aneurysms, sepsis (SIRS), multiple organ failure (MODS, MOF), inflammation disorders of the kidney, chronic intestinal disorders (IBD, Crohn's Disease, UC), pancreatitis, peritonitis, rheumatoid disorders, inflammatory skin disorders and inflammatory eye disorders.

The salts according to the invention can furthermore be used for treatment and/or prophylaxis of asthmatic disorders of varying severity with intermittent or persistent characteristics (refractive asthma, bronchial asthma, allergic asthma, intrinsic asthma, extrinsic asthma, medicament- or dust-induced asthma), of various forms of bronchitis (chronic bronchitis, infectious bronchitis, eosinophilic bronchitis), of Bronchiolitis obliterans, bronchiectasis, pneumonia, idiopathic interstitial pneumonia, farmer's lung and related disorders, of coughs and colds (chronic inflammatory cough, iatrogenic cough), inflammation of the nasal mucosa (including medicament-related rhinitis, vasomotoric rhinitis and seasonal allergic rhinitis, for example hay fever) and of polyps.

The salts according to the invention are also suitable for treatment and/or prophylaxis of fibrotic disorders of the internal organs, for example the lung, the heart, the kidney, the bone marrow and in particular the liver, and also dermatological fibroses and fibrotic eye disorders. In the context of the present invention, the term "fibrotic disorders" encompasses particularly the following terms: hepatic fibrosis, cirrhosis of the liver, pulmonary fibrosis, endomyocardial fibrosis, cardiomyopathy, nephropathy, glomerulonephritis, interstitial renal fibrosis, fibrotic damage resulting from diabetes, bone marrow fibrosis and similar fibrotic disorders, scleroderma, morphea, keloids, hypertrophic scarring (also following surgical procedures), naevi, diabetic retinopathy and proliferative vitroretinopathy.

The salts according to the invention are also suitable for controlling postoperative scarring, for example as a result of glaucoma operations.

Furthermore, the salts according to the invention can also be used cosmetically for ageing and keratinized skin In addition, the salts of the invention can also be used for treatment and/or prophylaxis of dyslipidemias (hypercholesterolemia, hypertriglyceridemia, elevated concentrations of the postprandial plasma triglycerides, hypoalphalipoproteinemia, combined hyperlipidemias), nephropathy and neuropathy), cancers (skin cancer, brain tumors, breast cancer, bone marrow tumors, leukemias, liposarcomas, carcinoma of the gastrointestinal tract, of the liver, pancreas, lung, kidney, urinary tract, prostate and genital tract, and also malignant tumors in the lymphoproliferative system, for example Hodgkin's and non-Hodgkin's lymphoma), of disorders of the gastrointestinal tract and of the abdomen (glossitis, gingivitis, periodontitis, esophagitis, eosinophilic gastroenteritis, mastocytosis, Crohn's disease, colitis, proctitis, pruritus ani, diarrhea, celiac disease, hepatitis, chronic hepatitis, hepatic fibrosis, cirrhosis of the liver, pancreatitis and cholecystitis), skin disorders (allergic skin disorders, psoriasis, acne, eczema, neurodermitis, various forms of dermatitis, and also keratitis, bullosis, vasculitis, cellulitis, panniculitis, lupus elythematodes, erythema, lymphoma, skin cancer, Sweet's syndrome, Weber-Christian syndrome, scarring, warts, chilblains), of disorders of the skeletal bone and of the joints, and also of the skeletal muscle (various forms of arthritis, various forms of arthropathies, scleroderma and of further disorders with an inflammatory or immunological component, for example paraneoplastic syndrome, in the event of rejection reactions after organ transplants and for wound healing and angiogenesis, especially in the case of chronic wounds.

The salts according to the invention are additionally suitable for treatment and/or prophylaxis of ophthalmologic disorders, for example glaucoma, normotensive glaucoma, high intraocular pressure and combinations thereof, of age-related macular degeneration (AMD), of dry or non-exudative AMD, moist or exudative or neovascular AMD, choroidal neovascularization (CNV), detached retina, diabetic retinopathy, atrophic changes to the retinal pigment epithelium (RPE), hypertrophic changes to the retinal pigment epithelium (RPE), diabetic macular edema, retinal vein occlusion, choroidal retinal vein occlusion, macular edema, macular edema due to retinal vein occlusion, angiogenesis at the front of the eye, for example corneal angiogenesis, for example following keratitis, cornea transplant or keratoplasty, corneal angiogenesis due to hypoxia (extensive wearing of contact lenses), pterygium conjunctiva, subretinal edema and intraretinal edema.

In addition, the salts according to the invention are suitable for the treatment and/or prophylaxis of elevated and high intraocular pressure resulting from traumatic hyphema, periorbital edema, postoperative viscoelastic retention, intraocular inflammation, use of cortico steroids, pupillary block or idiopathic causes, and of elevated intraocular pressure following trabeculectomy and due to pre-operative conditions.

The present invention further provides for the use of the salts according to the invention for treatment and/or prophylaxis of disorders, especially the disorders mentioned above.

The present invention further provides for the use of the salts according to the invention for production of a medicament for treatment and/or prophylaxis of disorders, especially the disorders mentioned above.

The present invention further provides the salts according to the invention for use in a method for treatment and/or prophylaxis of heart failure, pulmonary hypertension, chronic obstructive pulmonary disease, asthma, kidney failure, nephropathy, fibrotic disorders of the internal organs and dermatological fibroses.

The present invention further provides medicaments which comprise at least one compound of the invention, typically together with one or more inert, nontoxic, pharmaceutically suitable excipients, and for the use thereof for the aforementioned purposes.

The salts of the invention can act systemically and/or locally. For this purpose, they can be administered in a suitable manner, for example by the oral, parenteral, pulmonal, nasal, sublingual, lingual, buccal, rectal, dermal, transdermal, conjunctival or otic route, or as an implant or stent.

The salts of the invention can be administered in administration forms suitable for these administration routes.

Suitable administration forms for oral administration are those which work according to the prior art and release the compounds of the invention rapidly and/or in a modified manner and which contain the compounds of the invention in crystalline and/or amorphized and/or dissolved form, for example tablets (uncoated or coated tablets, for example with gastric juice-resistant or retarded-dissolution or insoluble coatings which control the release of the compound of the invention), tablets or films/oblates which disintegrate rapidly in the oral cavity, films/lyophilizates, capsules (for example hard or soft gelatin capsules), sugar-coated tablets, granules, pellets, powders, emulsions, suspensions, aerosols or solutions.

Parenteral administration can bypass an absorption step (e.g. intravenously, intraarterially, intracardially, intraspinally or intralumbally) or include an absorption (e g inhalatively, intramuscularly, subcutaneously, intracutaneously, percutaneously or intraperitoneally) Administration forms suitable for parenteral administration include preparations for injection and infusion in the form of solutions, suspensions, emulsions, lyophilizates or sterile powders.

For the other administration routes, suitable examples are inhalation medicaments (including powder inhalers, nebulizers, aerosols), nasal drops, solutions or sprays; tablets for lingual, sublingual or buccal administration, films/oblates or capsules, suppositories, ear or eye preparations, vaginal capsules, aqueous suspensions (lotions, shaking mixtures), lipophilic suspensions, ointments, creams, transdermal therapeutic systems (e.g. patches), milk, pastes, foams, dusting powders, implants or stents.

Oral and parenteral administration are preferred, especially oral, intravenous and inhalative administration.

The salts of the invention can be converted to the administration forms mentioned. This can be done in a manner known per se, by mixing with inert, nontoxic, pharmaceutically suitable excipients. These excipients include carriers (for example microcrystalline cellulose, lactose, mannitol), solvents (e.g. liquid polyethylene glycols), emulsifiers and dispersing or wetting agents (for example sodium dodecylsulfate, polyoxysorbitan oleate), binders (for example polyvinylpyrrolidone), synthetic and natural polymers (for example albumin), stabilizers (e.g. antioxidants, for example ascorbic acid), colorants (e.g. inorganic pigments, for example iron oxides) and flavor and/or odor correctants.

In general, it has been found to be advantageous in the case of parenteral administration to administer amounts of about 0.001 to 1 mg/kg, preferably about 0.01 to 0.5 mg/kg, of body weight to achieve effective results. In the case of oral administration the dosage is about 0.01 to 100 mg/kg, preferably about 0.01 to 20 mg/kg and most preferably 0.1 to 10 mg/kg of body weight.

The invention furthermore provides a process for preparing the salts according to the invention by dissolving the compound of the formula (I) in the form of the free acid for example in an inert solvent (optionally with addition of a cosolvent) and stirring or shaking with a solution of the salt-forming base at a temperature of 10° C. to 60° C., preferably at 20° C. to 40° C., particularly preferably at 25° C. or at room temperature. The resulting crystals of the salts are separated off and the solvent present is removed by drying to constant weight at room temperature or elevated temperature.

Suitable inert solvents are lower alcohols such as methanol, ethanol, n-propanol, isopropanol, n-butanol, sec-butanol, isobutanol, 1-pentanol, ketones such as acetone, alkanes such as n-pentane, cyclopentane, n-hexane, cyclohexane, or tetrahydrofuran, acetonitrile, toluene, ethyl acetate, 1,4-dioxane or mixtures of the solvents mentioned. Preference is given to acetonitrile, toluene and isopropanol or mixtures of the solvents mentioned.

Optionally, a cosolvent may be employed. Suitable for this purpose are acetonitrile, acetone, 2-propanol, isopropyl acetate, 2-methyltetrafuran, toluene, 1,4-dioxane or else mixtures thereof. Depending on the salt-forming base used, preference is given to toluene, isopropyl acetate or acetonitrile.

Suitable salt-forming bases are, in principle, sodium hydroxide, potassium hydroxide, choline bicarbonate, ammonium carbonate, sodium carbonate, potassium carbonate, L-lysine, tris(hydroxymethyl)aminomethane, N-methyl-D-glucamine, L-arginine, sodium bicarbonate or potassium bicarbonate. According to the invention, L-lysine, sodium bicarbonate and potassium bicarbonate have been found to be particularly suitable for salt formation.

The preparation processes are generally carried out under atmospheric pressure. However, it is also possible to operate under elevated or reduced pressure, for example at from 0.5 to 5 bar.

Unless stated otherwise, the percentages in the tests and examples which follow are percentages by weight; parts are parts by weight. Solvent ratios, dilution ratios and concentration data for the liquid/liquid solutions are based in each case on volume.

EXPERIMENTAL PART

The X-ray diffractograms were recorded at room temperature using an X'Pert PRO (PANalytical) XRD transmission/reflection diffractometer (radiation: copper, Kα1, wavelength: 1.5406 Å). There was no sample preparation.

WORKING EXAMPLES

Preparation of the Compound of the Formula (I) (Free Acid)

(S)-4-Trifluoromethylindan-1-ol

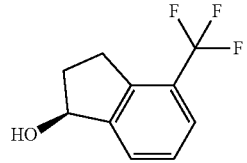 [SMILES: O[C@H]1CCc2c1cccc2C(F)(F)F]

Under argon, a solution of 55.7 g (278.3 mmol) of 4-trifluoromethyl-1-indanone, 194 ml (1.391 mol) of triethyl-amine and 1.60 g (2.50 mmol) of RuCl(p-cymene)[(S,S)-TsDPEN] (CAS No.: 192139-90-5; IUPAC name: (S,S)—N-(p-toluenesulphonyl)-1,2-diphenylethanediamino (chloro) [1-methyl-4-(propan-2-yl)benzene]ruthenium(II)) in 258 ml of dichloromethane was heated to 35° C. and, at this temperature, 52.5 ml (1.391 mol) of formic acid were added gradually (addition time about 40 min). During the addition, the temperature of the reaction mixture increased to 42° C. After the addition was complete, the mixture was stirred at 38° C. for a further 2 h. All volatile constituents were removed on a rotary evaporator and under HV. Subsequently, the residue was dissolved in a little dichloromethane and purified using 1 kg of silica gel (eluent:first 3 liters of cyclohexane/ethyl acetate 5:1, then 6 liters of cyclohexane/ethyl acetate 1:1). The suitable fractions were concentrated on a rotary evaporator and the product was dried under HV. This gave 51.2 g (90% of theory) of the title compound.

$^1$H-NMR (400 MHz, DMSO-d$_6$): δ [ppm]=1.76-1.91 (m, 1H), 2.40 (ddt, 1H), 2.86 (dt, 1H), 3.01-3.13 (m, 1H), 5.09 (q, 1H), 5.45 (d, 1H), 7.38-7.48 (m, 1H), 7.55 (d, 1H), 7.62 (d, 1H).

Ethyl 1-(3-methyl-2-oxo-2,3-dihydro-1,3-benzoxazol-6-yl)-2,4-dioxo-1,2,3,4-tetrahydropyrimidine-5-carboxylate

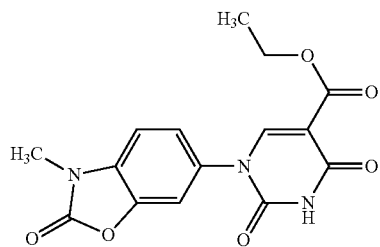 [SMILES: CCOC(=O)c1cn(-c2ccc3c(c2)oc(=O)n3C)c(=O)[nH]c1=O]

40.0 g (243.7 mmol) of 6-amino-3-methyl-1,3-benzoxazol-2(3H)-one were initially charged in 2.5 l of ethanol, and 63.2 g (243.7 mmol) of ethyl 3-ethoxy-2-[(ethoxycarbonyl)carbamoyl]acrylate (for preparation see: Senda, Shigeo; Hirota, Kosaku; Notani, Jiyoji, Chemical & Pharmaceutical Bulletin (1972), 20(7), 1380-8) were added. After a few minutes, a thick suspension formed. This mixture was heated to reflux temperature for 1.5 h. After cooling slightly (about 60° C.), 27.3 g (243.7 mmol) of potassium tert-butoxide were added and the reaction mixture was stirred further at reflux temperature for 4.5 h. For workup, the reaction suspension was cooled slightly (about 60° C.), then stirred into about 10 liters of cold 1N hydrochloric acid. The solid was filtered off with suction, washed with water and dried in a vacuum drying cabinet at 70° C. overnight. This gave 64.0 g (79% of theory) of the title compound.

LC-MS (Method 1): $R_t$=0.59 min; MS (ESIpos): m/z=332 (M+H)$^+$.

$^1$H-NMR (400 MHz, DMSO-d$_6$): δ [ppm]=1.22 (t, 3H), 3.38 (s, 3H), 4.17 (q, 2H), 7.38 (s, 2H), 7.59 (s, 1H), 8.26 (s, 1H), 11.69 (s, 1H).

Ethyl 1-(3-methyl-2-oxo-2,3-dihydro-1,3-benzoxazol-6-yl)-2,4-dioxo-3-[(1R)-4-(trifluoromethyl)-2,3-dihydro-1H-inden-1-yl]-1,2,3,4-tetrahydropyrimidine-5-carboxylate (R enantiomer)

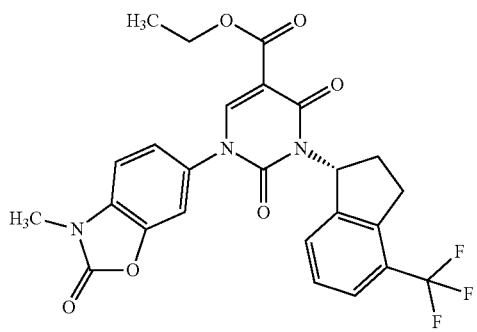 [SMILES: CCOC(=O)c1cn(-c2ccc3c(c2)oc(=O)n3C)c(=O)n([C@@H]2CCc3c2cccc3C(F)(F)F)c1=O]

Method A: Under argon, a solution of 200 mg (0.60 mmol) of ethyl 1-(3-methyl-2-oxo-2,3-dihydro-1,3-benzoxazol-6-yl)-2,4-dioxo-1,2,3,4-tetrahydropyrimidine-5-carboxylate (see above) and 475 mg (1.81 mmol) of triphenylphosphine in THF/DMF 1:1 (7.6 ml) was cooled to −30° C. 238 μl (1.20 mmol) of diisopropyl azodicarboxylate were added dropwise and then a solution of 146 mg (0.69 mmol) of (1S)-4-(trifluoromethyl)indan-1-ol (see above) in about 1 ml of THF was added dropwise. The reaction mixture was warmed to room temperature and stirred at room temperature for 30 min. For workup, the mixture was cooled to 0° C., 5 ml of 1M hydrochloric acid were added and the mixture was warmed to room temperature and stirred for 30 min. The mixture was then extracted with ethyl acetate. The organic phase was washed twice with 1M hydrochloric acid and once with saturated sodium chloride solution, dried over magnesium sulfate and concentrated under reduced pressure. The residue was subjected to extractive stirring with ethanol, and the precipitated solid was filtered off with suction and discarded. The filtrate was concentrated, dissolved in a little dichloromethane and purified by flash chromatography (dichloromethane/methanol 120:1→20:1). This gave 135 mg (43% of theory) of the title compound in about 95% purity.

LC-MS (Method 1): $R_t$=1.13 min; m/z=516 (M+H)$^+$.

$^1$H-NMR (400 MHz, DMSO-d6): δ [ppm]=1.22 (t, 3H), 2.37-2.43 (m, 1H), 2.43-2.48 (m, 1H, partially obscured by DMSO signal), 3.03-3.14 (m, 1H), 3.22-3.30 (m, 1H, partially obscured by water signal), 3.38 (s, 3H), 4.18 (q, 2H), 6.34-6.56 (m, 1H), 7.32-7.43 (m, 3H), 7.45-7.50 (m, 1H), 7.53 (d, 1H), 7.55-7.64 (m, 1H), 8.35 (s, 1H).

In an analogous experiment, it was possible to isolate a fraction with 99% purity. For this batch, the specific optical rotation measured was:

Specific optical rotation: $α_D^{20}$=+132.9°, (chloroform, c=0.395 g/100 ml).

Method B: Under argon, a solution of 5.0 g (15.1 mmol) of ethyl 1-(3-methyl-2-oxo-2,3-dihydro-1,3-benzoxazol-6-yl)-2,4-dioxo-1,2,3,4-tetrahydropyrimidine-5-carboxylate (see above), 6.73 g (25.7 mmol) of triphenylphosphine and 3.66 g (18.1 mmol) of (1S)-4-(trifluoromethyl)indan-1-ol (see above) was initially charged in 240 ml of DMF/THF 2:1 (v/v) and cooled to −15° C. 4.76 ml (24.15 mmol) of diisopropyl azodicarboxylate was slowly added dropwise at such a rate that the temperature of the reaction mixture did not rise above −10° C. At the end of the addition, the mixture was stirred at −10° C. for another 1 h, then warmed to room temperature and poured onto 1.3 l of water. The mixture was extracted twice with 300 ml each time of ethyl acetate. The combined organic phases were washed with a saturated sodium chloride solution, dried over magnesium sulfate and freed of the solvent on a rotary evaporator. The residue (18 g) was purified in two chromatography steps: first using a 200 g silica gel column with dichloromethane/acetone 97.5:2.5 as the mobile phase. The resulting product-containing fractions were concentrated and the residue was applied again to a 200 g silica gel column. 2.5 l of cyclohexane/ethyl acetate 1:1 as mobile phase were used to elute further impurities, then the desired product was eluted from the column with dichloromethane/methanol 95:5. This gave 3.40 g (44% of theory) of the title compound in 95% purity (the NMR showed about 5% ethyl acetate). A further 920 mg were obtainable by a new purification of a mixed fraction. Total yield: 4.32 g (56% of theory).

LC-MS (Method 1): $R_t$=1.15 min; m/z=516 (M+H)$^+$.

$^1$H-NMR (400 MHz, CD$_2$Cl$_2$): δ [ppm] =1.31 (t, 3H), 2.37-2.49 (m, 1H), 2.59 (dtd, 1H), 3.14 (dt, 1H), 3.40 (s, 3H), 3.42-3.53 (m, 1H), 4.29 (q, 2H), 6.54-6.68 (m, 1H), 7.06 (d, 1H), 7.17 (d, 1H), 7.22 (s, 1H), 7.26-7.36 (m, 2H), 7.49 (d, 1H), 8.28 (s, 1H).

Chiral analytical HPLC (Method 25): $R_t$=7.49 min; 99% ee

1-(3-Methyl-2-oxo-2,3-dihydro-1,3-benzoxazol-6-yl)-2,4-dioxo-3-[(1R)-4-(trifluoromethyl)-2,3-dihydro-1H-inden-1-yl]-1,2,3,4-tetrahydropyrimidine-5-carboxylic acid (R enantiomer)

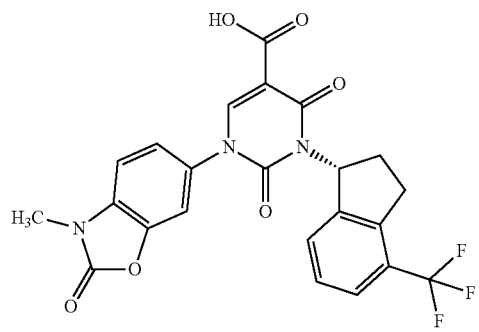 [SMILES: Cn1c(=O)oc2cc(-n3cc(C(=O)O)c(=O)n([C@@H]4CCc5c4cccc5C(F)(F)F)c3=O)ccc21]

3.40 g (6.60 mmol) of ethyl 1-(3-methyl-2-oxo-2,3-dihydro-1,3-benzoxazol-6-yl)-2,4-dioxo-3-[(1R)-4-(trifluoromethyl)-2,3-dihydro-1H-inden-1-yl]-1,2,3,4-tetrahydropyrimidine-5-carboxylate (see above) were stirred in 44 ml of glacial acetic acid and 22 ml of concentrated hydrochloric acid at reflux temperature for 1 h. After cooling slightly (about 60° C.), the mixture was fully concentrated under reduced pressure. 50 ml of isopropanol were added to the amorphous residue and the mixture was heated to reflux for 15 min, in the course of which a solid formed. The suspension was then cooled to 10° C. and then the solid was filtered off with suction. The solid was washed twice with 15 ml each time of isopropanol, filtered off with suction and dried under high vacuum. This gave 2.53 g (79% of theory) of the title compound.

LC-MS (Method 1): $R_t$=1.12 min; m/z=488 (M+H)$^+$.

Chiral analytical HPLC (Method 14): $R_t$=13.3 min; about 99% ee $^1$H-NMR (400 MHz, CD$_2$Cl$_2$): δ [ppm]=2.40-2.52 (m, 1H), 2.59-2.72 (m, 1H), 3.12-3.25 (m, 1H), 3.41 (s, 3H), 3.44-3.56 (m, 1H), 6.58-6.69 (m, 1H), 7.04-7.11 (m, 1H), 7.15-7.21 (m, 1H), 7.24 (br.s, 1H), 7.29-7.38 (m, 2H), 7.53 (s, 1H), 8.54 (s, 1H), 12.39 (br. s, 1H).

Specific rotation $\alpha_D^{20}$=+135.3° (methanol, c=0.43).

In an analogous experiment, the specific rotation of the product was measured in chloroform: $\alpha_D^{20}$=+159.5° (chloroform, c=0.395).

An X-ray structure analysis in the complex with chymase confirmed the R configuration for this enantiomer.

Example 1

Preparation of the L-lysine salt of 1-(3-methyl-2-oxo-2,3-dihydro-1,3-benzoxazol-6-yl)-2,4-dioxo-3-[(1R)-4-(trifluoromethyl)-2,3-dihydro-1H-inden-1-yl]-1,2,3,4-tetrahydropyrimidine-5-carboxylic acid About 300 mg of 1-(3-methyl-2-oxo-2,3-dihydro-1,3-benzoxazol-6-yl)-2,4-dioxo-3-[(1R)-4-(trifluoromethyl)-2,3-dihydro-1H-inden-1-yl]-1,2,3,4-tetrahydropyrimidine-5-carboxylic acid (free acid) were dissolved in 30 ml of acetonitrile. With pivoting, 30 ml of toluene were added as cosolvent. A solution of 90 mg of L-lysine in 10 ml of water was then added, and the mixture was stirred at room temperature overnight. The suspension was then filtered and the residue was dried at room temperature and ambient humidity. The residue was examined by X-ray diffractometry and corresponds to the title compound.

Example 2

Preparation of the sodium salt of 1-(3-methyl-2-oxo-2,3-dihydro-1,3-benzoxazol-6-yl)-2,4-dioxo-3-[(1R)-4-(trifluoromethyl)-2,3-dihydro-1H-inden-1-yl]-1,2,3,4-tetrahydropyrimidine-5-carboxylic acid About 300 mg of 1-(3-methyl-2-oxo-2,3-dihydro-1,3-benzoxazol-6-yl)-2,4-dioxo-3-[(1R)-4-(trifluoromethyl)-2,3-dihydro-1H-inden-1-yl]-1,2,3,4-tetrahydropyrimidine-5-carboxylic acid (free acid) were dissolved in 30 ml of acetonitrile. With pivoting, 30 ml of isopropyl acetate were added as cosolvent. A solution of 65.2 mg of sodium bicarbonate in 10 ml of water was then added, and the mixture was stirred at room temperature for 60 min. The suspension was then filtered and the residue was dried at room temperature and ambient humidity. The residue was examined by X-ray diffractometry and corresponds to the title compound.

Example 3

Preparation of the potassium salt of 1-(3-methyl-2-oxo-2,3-dihydro-1,3-benzoxazol-6-yl)-2,4-dioxo-3-[(1R)-4-(trifluoromethyl)-2,3-dihydro-1H-inden-1-yl]-1,2,3,4-tetrahydropyrimidine-5-carboxylic acid About 300 mg of 1-(3-methyl-2-oxo-2,3-dihydro-1,3-benzoxazol-6-yl)-2,4-dioxo-3-[(1R)-4-(trifluoromethyl)-2,3-dihydro-1H-inden-1-yl]-1,2,3,4-tetrahydropyrimidine-5-carboxylic acid (free acid) were dissolved in 30 ml of acetonitrile. With pivoting, a further 30 ml of acetonitrile were added. A solution of 85.1 mg of potassium bicarbonate in 10 ml of water was then added, and the mixture was stirred at room temperature for 60 min. The suspension was then filtered and the residue was dried at room temperature and ambient humidity. The residue was examined by X-ray diffractometry and corresponds to the title compound.

TABLE 1

X-ray diffractometry of the free acid of 1-(3-methyl-2-oxo-2,3-dihydro-1,3-benzoxazol-6-yl)-2,4-dioxo-3-[(1R)-4-(trifluoromethyl)-2,3-dihydro-1H-inden-1-yl]-1,2,3,4-tetrahydropyrimidine-5-carboxylic acid and its salts
Peak maximum [2 theta]

| Lysine salt | Sodium salt | Potassium salt |
| --- | --- | --- |
| 6.1 | 3.6 | 6.0 |
| 9.9 | 4.3 | 6.5 |
| 10.9 | 5.3 | 9.4 |
| 12.2 | 5.9 | 10.4 |
| 14.1 | 6.0 | 11.2 |
| 14.9 | 7.2 | 12.0 |
| 16.2 | 8.0 | 13.0 |
| 16.7 | 8.6 | 15.3 |
| 16.9 | 9.0 | 16.5 |
| 18.5 | 9.6 | 16.8 |
| 18.7 | 10.6 | 18.0 |
| 19.2 | 10.9 | 18.5 |
| 20.0 | 11.3 | 19.2 |
| 21.6 | 11.8 | 19.8 |
| 22.3 | 12.8 | 20.5 |
| 22.7 | 13.0 | 21.1 |
| 23.0 | 13.5 | 21.7 |
| 24.4 | 14.1 | 22.7 |
| 24.4 | 14.5 | 23.7 |
| 24.8 | 15.5 | 24.2 |
| 25.7 | 16.0 | 25.2 |

TABLE 1-continued

X-ray diffractometry of the free acid of 1-(3-methyl-2-oxo-2,3-dihydro-1,3-benzoxazol-6-yl)-2,4-dioxo-3-[(1R)-4-(trifluoromethyl)-2,3-dihydro-1H-inden-1-yl]-1,2,3,4-tetrahydropyrimidine-5-carboxylic acid and its salts
Peak maximum [2 theta]

| Lysine salt | Sodium salt | Potassium salt |
| --- | --- | --- |
| 26.9 | 17.1 | 27.3 |
| 27.1 | 17.6 | 28.2 |
| 27.8 | 17.9 | 28.8 |
| 29.5 | 18.1 | 30.0 |
| 30.1 | 18.6 | 31.2 |
| 30.3 | 18.9 | 31.5 |
| 30.9 | 19.1 | 34.0 |
| 31.4 | 19.6 | 36.1 |
| 32.1 | 20.3 | |
| 33.1 | 20.9 | |
| 33.4 | 21.6 | |
| 33.8 | 22.0 | |
| 34.2 | 22.5 | |
| 35.0 | 23.5 | |
| 35.6 | 23.8 | |
| 36.1 | 24.3 | |
| 37.0 | 24.7 | |
| 37.5 | 25.1 | |
| | 25.8 | |
| | 27.1 | |
| | 27.8 | |
| | 28.5 | |
| | 29.0 | |
| | 29.1 | |
| | 30.1 | |
| | 30.4 | |
| | 30.8 | |
| | 31.7 | |

Figure 1:
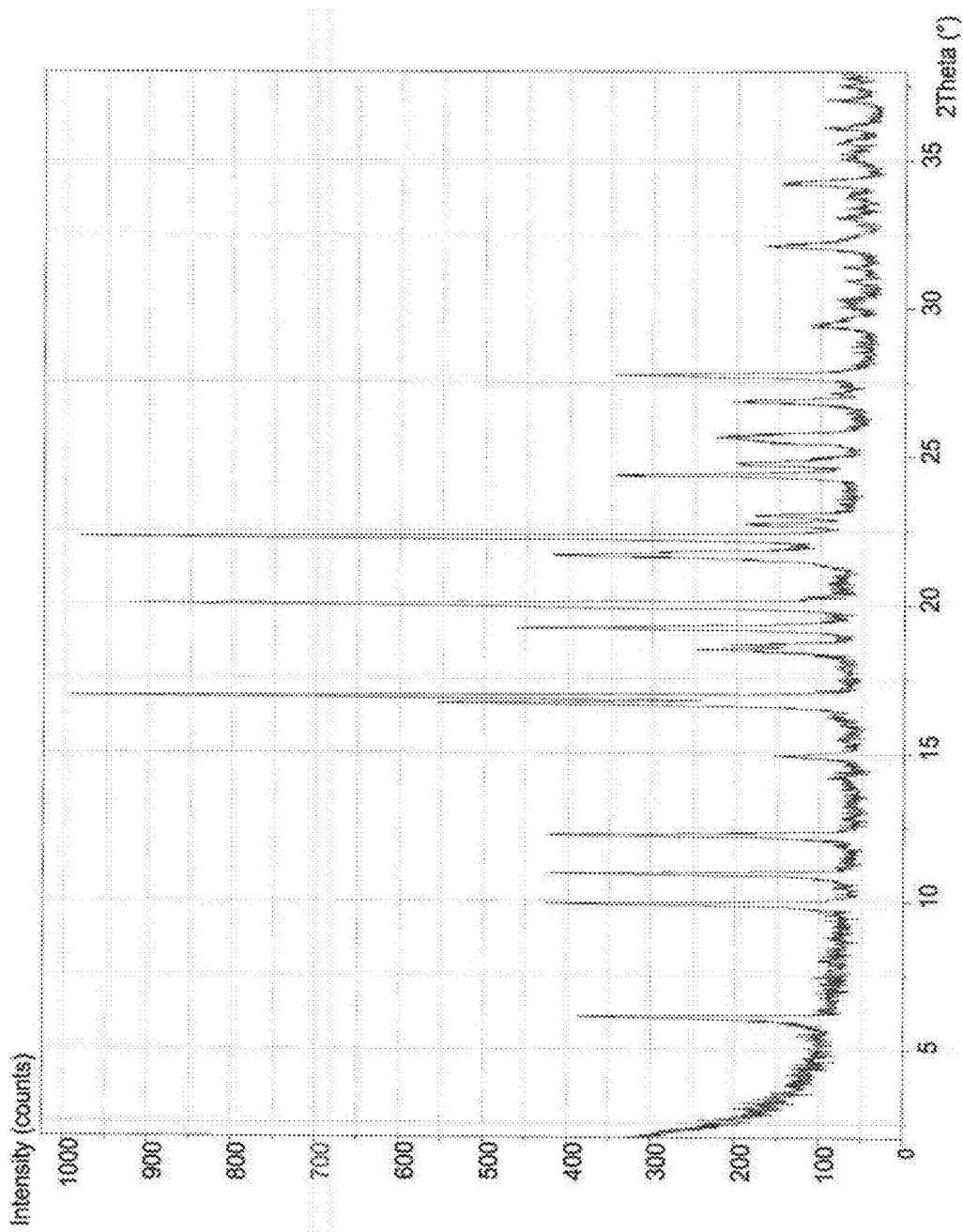
FIG. 1: X-ray diffractogram of the L-lysine salt of 1-(3-methyl-2-oxo-2,3-dihydro-1,3-benzoxazol-6-yl)-2,4-dioxo-3-[(1R)-4-(trifluoromethyl)-2,3-dihydro-1H-inden-1-yl]-1,2,3,4-tetrahydropyrimidine-5-carboxylic acid
Figure 2:
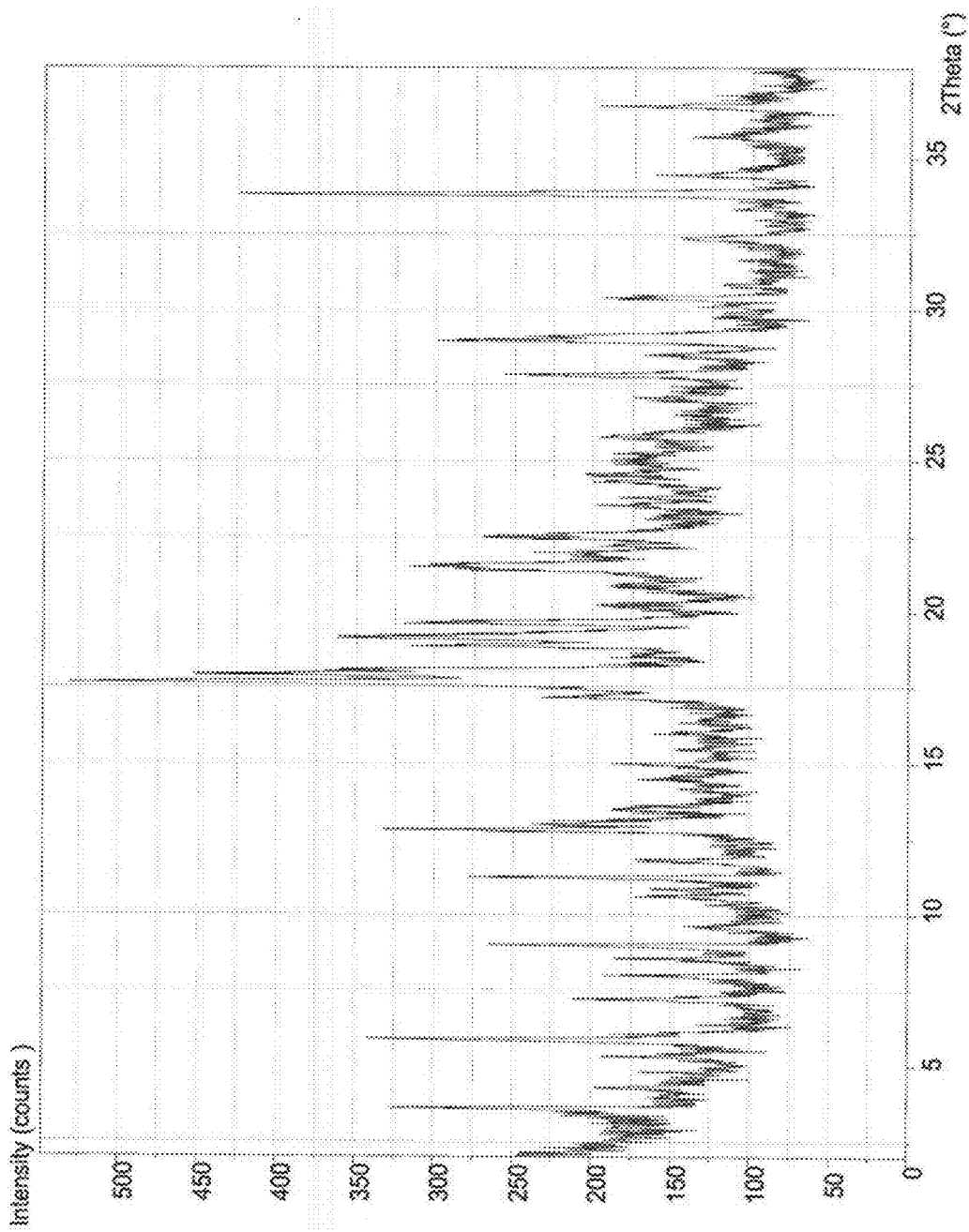
FIG. 2: X-ray diffractogram of the sodium salt of 1-(3-methyl-2-oxo-2,3-dihydro-L3-benzoxazol-6-yl)-2,4-dioxo-3-[(1R)-4-(trifluoromethyl)-2,3-dihydro-1H-inden-1-yl]-1,2,3,4-tetrahydropyrimidine-5-carboxylic acid
Figure 3:
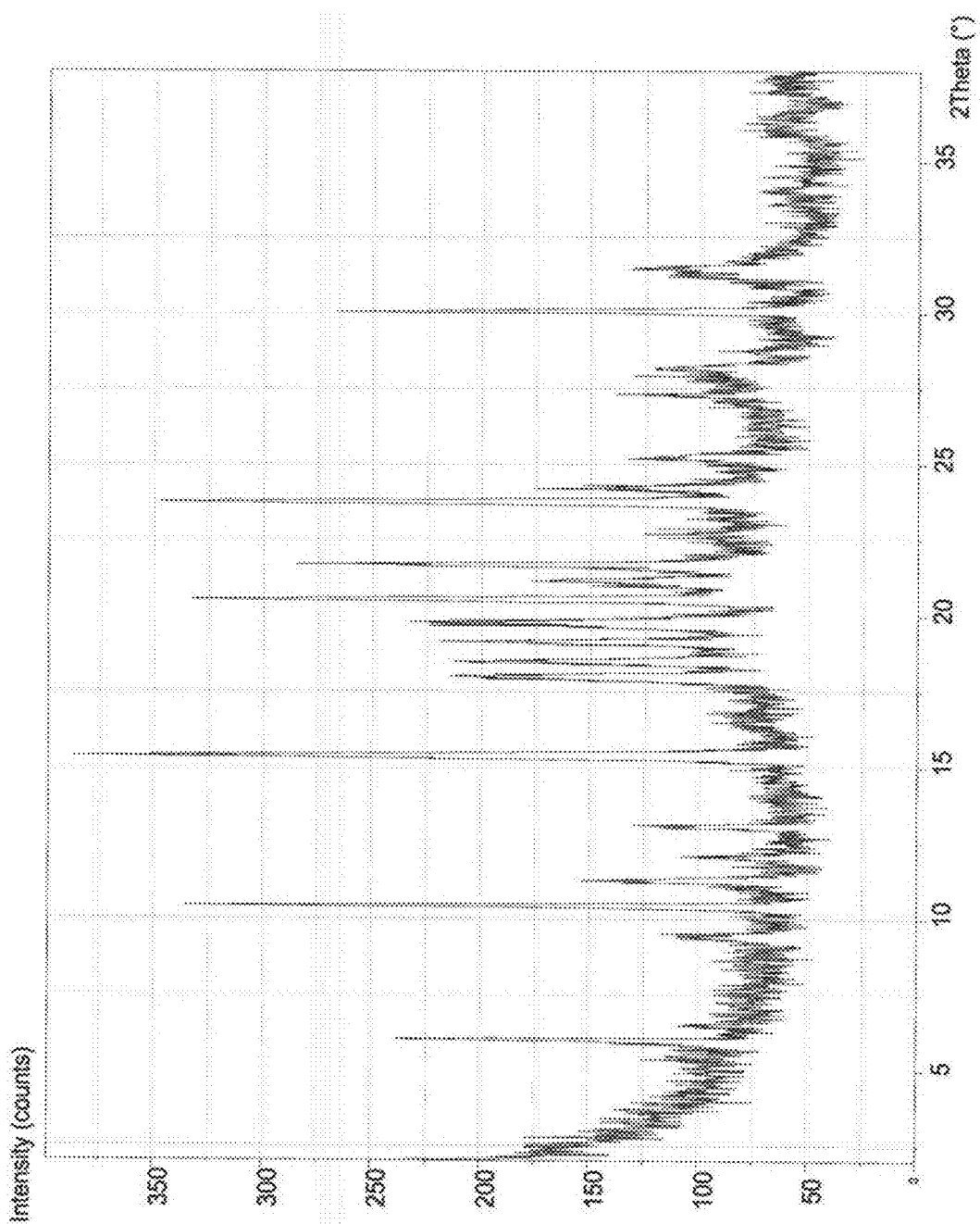
FIG. 3: X-ray diffractogram of the potassium salt of 1-(3-methyl-2-oxo-2,3-dihydro-L3-benzoxazol-6-yl)-2,4-dioxo-3-[(1R)-4-(trifluoromethyl)-2,3-dihydro-1H-inden-1-yl]-1,2,3,4-tetrahydropyrimidine-5-carboxylic acid

The invention claimed is:

1. A salt of a compound of formula (I), wherein the compound is 1-(3-methyl-2-oxo-2,3-dihydro-1,3-benzoxazol-6-yl)-2,4-dioxo-3-[(1R)-4-(trifluoromethyl)-2,3-dihydro-1H-inden-1-yl]-1,2,3,4-tetrahydropyrimidine-5-carboxylic acid

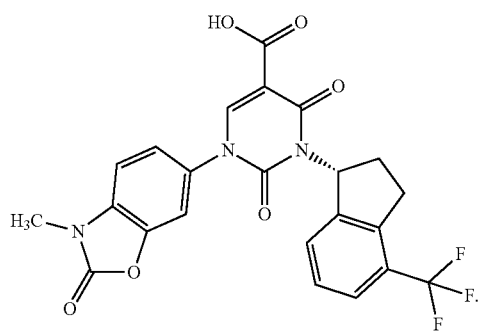

2. The salt of claim 1, wherein it is an amino acid salt or alkali metal salt.

3. The salt of claim 1 wherein it is a lysine salt.

4. The salt of claim 1 wherein it is the L-lysine salt.

5. The salt of claim 4, wherein the X-ray diffractogram of the compound has a peak maximum of the 2 theta angle at 16.9.

6. The salt of claim 4, wherein the X-ray diffractogram of the compound has peak maxima of the 2 theta angle at 16.9, 22.3 and 20.0.

7. The salt of claim 1, wherein it is a sodium salt.

8. The salt of claim 7, wherein the X-ray diffractogram of the compound has a peak maximum of the 2 theta angle at 17.6.

9. The salt of claim 7, wherein the X-ray diffractogram of the compound has peak maxima of the 2 theta angle at 17.6, 17.9 and 19.1.

10. The salt of claim 1, wherein it is a potassium salt.

11. The salt of claim 10, wherein the X-ray diffractogram of the compound has a peak maximum of the 2 theta angle at 23.7.

12. The salt of claim 10, wherein the X-ray diffractogram of the compound has peak maxima of the 2 theta angle at 23.7, 15.3 and 20.5.

13. A pharmaceutical formulation comprising the salt of claim 1 and no greater proportions of any other form of the compound of the formula (I).

14. A pharmaceutical formulation comprising the salt of claim 1 in more than 90 percent by weight based on the total amount of the compound of the formula (I) present.

15. A method of preparing the salt of claim 1, which comprises dissolving the compound of the formula (I) in the form of the free acid in an inert solvent and stirring or shaking with a solution of the salt-forming base at a temperature of 10° C. to 60° C.

16. A method of treating a disorder in a human, wherein the disorder is responsive to chymase inhibition and wherein the disorder is selected from the group consisting of a cardiovascular disorder, a kidney disorder, an inflammatory disorder, an allergic disorder and a fibrotic disorder, comprising administering to the human an effective amount of the salt of claim 1.

17. The method of claim 16, wherein the disorder is a cardiovascular disorder.

18. The method of claim 17, wherein the cardiovascular disorder is selected from the group consisting of atherosclerosis, peripheral vascular disorder, cardiac vascular disorder, micro- and macrovascular damage, vasculitis, restenosis, and endothelial dysfunction.

19. The method of claim 16, wherein the disorder is a kidney disorder.

20. The method of claim 19, wherein the kidney disorder is selected from the group consisting of acute renal insufficiency, chronic renal insufficiency, acute kidney failure, and chronic kidney failure.

21. The method of claim 16, wherein the disorder is heart failure, pulmonary hypertension, chronic obstructive pulmonary disease, asthma, kidney failure, nephropathy, a fibrotic disorder of internal organs or dermatological fibroses.

* * * * *